United States Patent
Dasch et al.

(10) Patent No.: US 6,558,702 B2
(45) Date of Patent: May 6, 2003

(54) METHOD OF MODIFYING THE RELEASE PROFILE OF SUSTAINED RELEASE COMPOSITIONS

(75) Inventors: James R. Dasch, Needham, MA (US); M. Gary I. Riley, Cambridge, MA (US)

(73) Assignee: Alkermes Controlled Therapeutics, Inc., Cambridge, MA (US)

( * ) Notice: Subject to any disclaimer, the term of this patent is extended or adjusted under 35 U.S.C. 154(b) by 0 days.

(21) Appl. No.: 09/835,001

(22) Filed: Apr. 13, 2001

(65) Prior Publication Data

US 2003/0004100 A1 Jan. 2, 2003

(51) Int. Cl.$^7$ .............................. A61K 9/14; A61K 9/52; A61K 31/7052; A61K 38/02; A61K 38/18
(52) U.S. Cl. ...................... 424/484; 424/422; 424/423; 424/486; 424/489; 424/499; 424/501; 514/2; 514/21; 514/44; 514/89; 514/107; 514/108; 514/964
(58) Field of Search ................................. 514/2, 12, 21, 514/44, 89, 107, 108, 772, 788, 964, 965; 424/851, 422, 423, 424, 425, 426, 484, 485, 486, 487, 488, 489, 490, 491, 492, 493, 494, 495, 496, 497, 498, 499, 500, 501, 502

(56) References Cited

U.S. PATENT DOCUMENTS

| | | | |
|---|---|---|---|
| 3,523,906 A | 8/1970 | Vrancken et al. | 252/316 |
| 3,691,090 A | 9/1972 | Kitajima et al. | 252/316 |
| 3,737,337 A | 6/1973 | Schnoring et al. | 117/100 |
| 3,891,570 A | 6/1975 | Fukushima et al. | 252/316 |
| 3,960,757 A | 6/1976 | Morishita et al. | 252/316 |
| 4,327,039 A | 4/1982 | Blum et al. | 260/502.5 |
| 4,389,330 A | 6/1983 | Tice et al. | 427/213.36 |
| 4,705,651 A | 11/1987 | Staibano | 260/502.5 |

(List continued on next page.)

FOREIGN PATENT DOCUMENTS

| | | | |
|---|---|---|---|
| EP | 709085 | * | 5/1996 |
| WO | WO 97/07788 | | 3/1997 |

OTHER PUBLICATIONS

Vyavahare et al. Synergism of calcium–ethanehydroxybisphosphonate. . . Journal of Controlled Release. 1995, vol. 34, pp. 97–108.*

Dunn, C.J. et al., "Demonstration of Novel Anti–Arthritic and Anti–Inflammatory Effects of Diphosphonates,", *Journal of Pharmacology and Experimental Therapeutics*, 266(3):1691–1698 (1993).

Van Gelder, J.M., et al., "In Vitro and Vivo Effects of Tetrakisphosphonates on Bone Resorption, Tumor Osteolysis, Ectopic Calcification, and Macrophages," *Journal of Pharmaceutical Sciences*, 86(3) :283–289 (1997).

Nugent, R.A., et al., "Pyrazoline Bisphosphonate Esters as Novel Antiinflammatory and Antiarthritic Agents," *J. Med. Chem.*, 36:134–139 (1993).

(List continued on next page.)

Primary Examiner—Jeffrey E. Russel
(74) Attorney, Agent, or Firm—Hamilton, Brook, Smith & Reynolds, P.C.

(57) ABSTRACT

The present invention relates to a method for the sustained release in vivo of a biologically active agent comprising administering to a subject in need of treatment an effective amount of a sustained release composition comprising a biocompatible polymer having the biologically active agent incorporated therein, and a bisphosphonate wherein the bisphosphonate compound is present in an amount sufficient to modify the release profile of the biologically active agent from the sustained release composition. Pharmaceutical compositions suitable for use in the method of the invention are also disclosed.

58 Claims, 8 Drawing Sheets

U.S. PATENT DOCUMENTS

| | | | |
|---|---|---|---|
| 4,746,654 A | 5/1988 | Breliere et al. | 514/108 |
| 4,922,007 A | 5/1990 | Kieczykowski et al. | 562/13 |
| 5,019,400 A | 5/1991 | Gombotz et al. | 424/497 |
| 5,019,651 A | 5/1991 | Kieczykowski | 562/13 |
| 5,196,409 A | 3/1993 | Breuer et al. | 514/108 |
| 5,312,954 A | 5/1994 | Breuer et al. | 558/161 |
| 5,412,141 A | 5/1995 | Nugent | 558/214 |
| 5,583,122 A | 12/1996 | Benedict et al. | 514/89 |
| 5,618,563 A | 4/1997 | Berde et al. | 424/501 |
| 5,654,010 A | 8/1997 | Johnson et al. | 424/502 |
| 5,656,297 A | 8/1997 | Bernstein et al. | 424/484 |
| 5,667,808 A | 9/1997 | Johnson et al. | 424/501 |
| 5,674,534 A | 10/1997 | Zale et al. | 424/501 |
| 5,700,485 A | 12/1997 | Berde et al. | 424/501 |
| 5,711,968 A | 1/1998 | Tracy et al. | 424/487 |
| 5,716,644 A | 2/1998 | Zale et al. | 424/497 |
| 5,773,477 A * | 6/1998 | MacLean et al. | 514/648 |
| 5,861,168 A * | 1/1999 | Cooke et al. | 424/424 |
| 5,885,973 A | 3/1999 | Papapoulos et al. | 514/106 |
| 5,916,597 A | 6/1999 | Lee et al. | 424/501 |
| 5,922,253 A | 7/1999 | Herbert et al. | 264/5 |
| 6,080,779 A | 6/2000 | Gasper et al. | 514/451 |
| 6,117,856 A | 9/2000 | Binderman et al. | 514/108 |
| 6,162,929 A | 12/2000 | Foricher et al. | 549/6 |
| 6,165,513 A | 12/2000 | Dansereau et al. | 424/490 |
| 6,399,592 B1 * | 6/2002 | Whiteford | 514/109 |

OTHER PUBLICATIONS

D'Souza, M.J., et al., "Macrophage Depletion by Albumin Microencapsulated Clodronate: Attenuation of Cytokine Release in Macrophage–Dependent Glomerulonephritis," *Drug Development and Industrial Pharmacy*, 25(5):591–596 (1999).

Nugent, R.A., et al., "Carbonyl–Containing Bisphosphonate Esters as Novel Antiinflammatory and Antiarthritic Agents," *J. Med. Chem.*, 37:4449–4454 (1994).

Hyvönen, P.M., and Kowolik, M.J., "Influence of Dichloromethylene Bisphosphonate on the in vitro Phagocytosis of Hydroxyapatite Particles by Rat Peritoneal Exudate Cells: An Electron Microscopic and Chemiluminescence Study," *Annals of the Rheumatic Diseases*, 51:203–209 (1992).

Barbier, A., et al., "Studies on the Chronic Phase of Adjuvant Arthritis: Effect of SR 41319, A New Diphosphonate," *Annals of the Rheumatic Diseases*, 45:67–74 (1986).

Van Rooijen, N., et al., "Transient Suppression of Macrophage Functions by Liposome–Encapsulated Drugs," *Trends in Biotechnology*, 15:178–185 (1997).

Reginster, J.Y., et al., "Prevention of Postmenopausal Bone Loss by Tiludronate," *The Lancet*, pp. 1469–1471, (1989, Dec. 23/30).

Bijovet, O.L.M., et al., "APD in Paget's Disease of Bone," *Arthritis and Rheumatism*, 23(10):1193–1204 (1980).

Francis, M.D., et al., "The Effects of Disodium Ehtane–1–Hydroxy–1, 1–Diphosphonate on Adjuvant Induced Arthritis in Rats," *Calc. Tiss. Res.*, 9(2):109–121 (1972).

Flora, L., "Comparative Antiinflammatory and Bone Protective Effects of Two Diphosphonates in Adjuvant Arthritis," *Arthritis and Rheumatism*, 22(4):340–346 (1979).

Francis, M.D., et al., "NE–58095: A Diphosphonate Which Prevents Bone Erosion and Preserves Joint Architecture in Experimental Arthritis," *Int. J. Tiss. Reac.*, XI(5):239–252 (1989).

Daoud, A.S., et al., "The Effect of Ethane–1–Hydroxy–1, 1–Diphosphonate (EHDP) on Necrosis of Atherosclerotic Lesions," *Atherosclerosis*, 67:41–48 (1987).

Camilleri, J.P. et al., "The Effect of Free and Liposome–Encapsulated Clondronate on the Hepatic Mononuclear Phagocyte System in the Rat," *Clin. Exp. Immunol.*, 99(2):269–275 (1995).

Biewenga, J., et al., "Macrophage Depletion in the Rat After Intraperitoneal Administration of Liposome–Encapsulated Clodronate: Depletion Kinetics and Accelerated Repopulation of Peritoneal and Omental Macrophages by Administration of Freund's Adjuvant," *Cell Tissue Res.*, 280(1):189–196 (1995).

Van Rooijen, N., et al., "Depletion and Repopulation of Macrophages in Spleen and Liver of Rat After Intravenous Treatment with Liposome–Encapsulated Dichloromethylene Diphosphonate," *Cell Tissue Res.*, 260(2):215–222 (1990).

Delemarre, F.G.A., et al., "Repopulation of Macrophages in Popliteal Lymph Nodes of Mice After Liposome–Medicated Depletion," *Journal of Leukocyte Biology*, 47(3):251–257 (1990).

Storm, T., et al., "Effect of Intermittent Cyclical Etidornate Therapy on the Bone Mass and Fracture Rate in Women with Postmenopausal Osteoporosis," *New England Journal of Medicine*, 322(18):1265–1271.

Ralston, S.H. et al., "A Double Blind Placebo–Controlled Trial of Diphosphonate (APD) Therapy in Rheumatoid Arthritis–Preliminary Results," *Calcified Tissue*, Supplement to vol. 42, p. A23, Abstract No. 90 (1988).

Markusse, H.M., et al., "Bisphosphonates in Collagen Arthritis," *Rheumatology International*, 9(6):281–283 (1990).

* cited by examiner

METHOD OF MODIFYING THE RELEASE PROFILE OF SUSTAINED RELEASE COMPOSITIONS

BACKGROUND OF THE INVENTION

Many illnesses or conditions require administration of a constant or sustained level of a medicament or biologically active agent to provide the most effective prophylactic or therapeutic. This may be accomplished through a multiple dosing regimen or by employing a system that releases the medicament in a sustained fashion.

Attempts to sustain medication levels include the use of biodegradable materials, such as polymeric matrices, containing the medicament. The use of these matrices, for example, in the form of microparticles or microcarriers, provides sustained release of medicaments by utilizing the inherent biodegradability of the polymer. The ability to provide a sustained level of medicament can result in improved patient compliance.

However, these sustained release devices can exhibit high release of active agent over the first twenty-four hours, often referred to as a burst. In some instances this burst can result in an undesirable increase in the levels of biologically active agent and minimal release of agent thereafter. In addition, due to the high solution concentration of medicament within and localized around these sustained release devices, the medicament can aggregate thereby increasing immunogenicity in vivo and interfering with the desired release profile for the medicament.

Therefore, a need exists to exert additional control over the release profile of sustained release compositions by, for example, reducing the burst of agent and/or providing an improved release such as a longer period of release.

SUMMARY OF THE INVENTION

The present invention is based upon the unexpected discovery that the release profile of a biologically active agent from a sustained release composition comprising a biocompatible polymer and the biologically active agent incorporated therein can be modified such as by prolonging the period of release of agent when a bisphosphonate compound is co-administered.

Accordingly, the present invention relates to a method for the sustained release in vivo of a biologically active agent comprising administering to a subject in need of treatment an effective amount of a sustained release composition comprising a biocompatible polymer having the biologically active agent incorporated therein, and a bisphosphonate wherein the bisphosphonate is present in an amount sufficient to modify the release profile of the biologically active agent from the sustained release composition.

In one embodiment, the bisphosphonate compound can be co-incorporated into the sustained release composition comprising the biocompatible polymer and the biologically active agent incorporated therein.

In another embodiment, the bisphosphonate compound can be separately incorporated into a second biocompatible polymer. The biocompatible polymer can be the same or different from the first biocompatible polymer which has the biologically active agent incorporated therein.

In yet another embodiment, the bisphosphonate compound can be present in an unencapsulated state but comingled with the sustained release composition. For example, the bisphosphonate can be solubilized in the vehicle used to deliver the sustained release composition. Alternatively, the bisphosphonate compound can be present as a solid suspended in an appropriate vehicle. Further, the bisphosphonate can be present as a powder which is comingled with the sustained release composition.

The invention described herein also relates to pharmaceutical compositions suitable for use in the invention. In one embodiment, the pharmaceutical composition comprises a sustained release composition comprising a biocompatible polymer having an effective amount of a biologically active agent incorporated therein, and an amount of bisphosphonate compound sufficient to modify the release profile of the biologically active agent from the sustained release composition.

In one embodiment, the bisphosphonate compound can be co-incorporated into the sustained release composition comprising the biocompatible polymer and the biologically active agent incorporated therein.

In another embodiment, the pharmaceutical composition comprises the sustained release composition comprising a first biocompatible polymer having incorporated therein an effective amount of a biologically active agent and a second biocompatible polymer having incorporated therein an amount of bisphosphonate which modifies the release profile of the biologically active agent from the first polymer. In a particular embodiment, the first and second polymers are the same type of polymer. In another embodiment, the first and second polymers are different.

In yet another embodiment, the bisphosphonate compound can be present in the pharmaceutical composition in an unencapsulated state. For example, the bisphosphonate compound can be comingled with the sustained release composition. In one embodiment, the bisphosphonate can be solubilized in the vehicle used to deliver the pharmaceutical composition. Alternatively, the bisphosphonate compound can be present as a solid suspended in an appropriate vehicle useful for delivering the pharmaceutical composition. Further, the bisphosphonate can be present as a powder which is comingled with the sustained release composition.

Without being bound by a particular theory, it is believed that at least in part the effects of the bisphosphonates can be related to a reduction in the amount of inflammatory cellular reaction which can occur in the area of administration of the sustained release composition. This reaction, although clinically insignificant, is well characterized as a foreign body response, and can be realized with most foreign materials.

The present invention also relates to a composition for the sustained release of bisphosphonates. The sustained release composition comprises a biocompatible polymer matrix having a therapeutically effective amount of bisphosphonate incorporated therein. Further, the invention relates to a method for the sustained release in vivo of a bisphosphonate compound comprising administering to a subject in need of treatment a therapeutically effective amount of a sustained release composition comprising a biocompatible polymer and a bisphosphonate compound.

In a particular embodiment, administration of the sustained release composition comprising a biocompatible polymer and a bisphosphonate can be to a joint, for example, the articular space of a joint. For example, the sustained release composition can be administered to the articular space of the knee, shoulder, ankle, hip etc . . .

The sustained release composition of the invention comprising a biocompatible polymer and a bisphosphonate compound can be used for the treatment of diseases associated with bone resorption or joint inflammation. For example, the sustained release composition having a biocompatible polymer and a bisphosphonate compound incorporated therein can be suitable for use as a treatment for rheumatoid arthritis, osteoporosis or Paget's disease.

BRIEF DESCRIPTION OF THE DRAWINGS

The foregoing and other objects, features and advantages of the invention will be apparent from the following more particular description of preferred embodiments of the invention, as illustrated in the accompanying drawings.

DETAILED DESCRIPTION OF THE INVENTION

Figure 1:
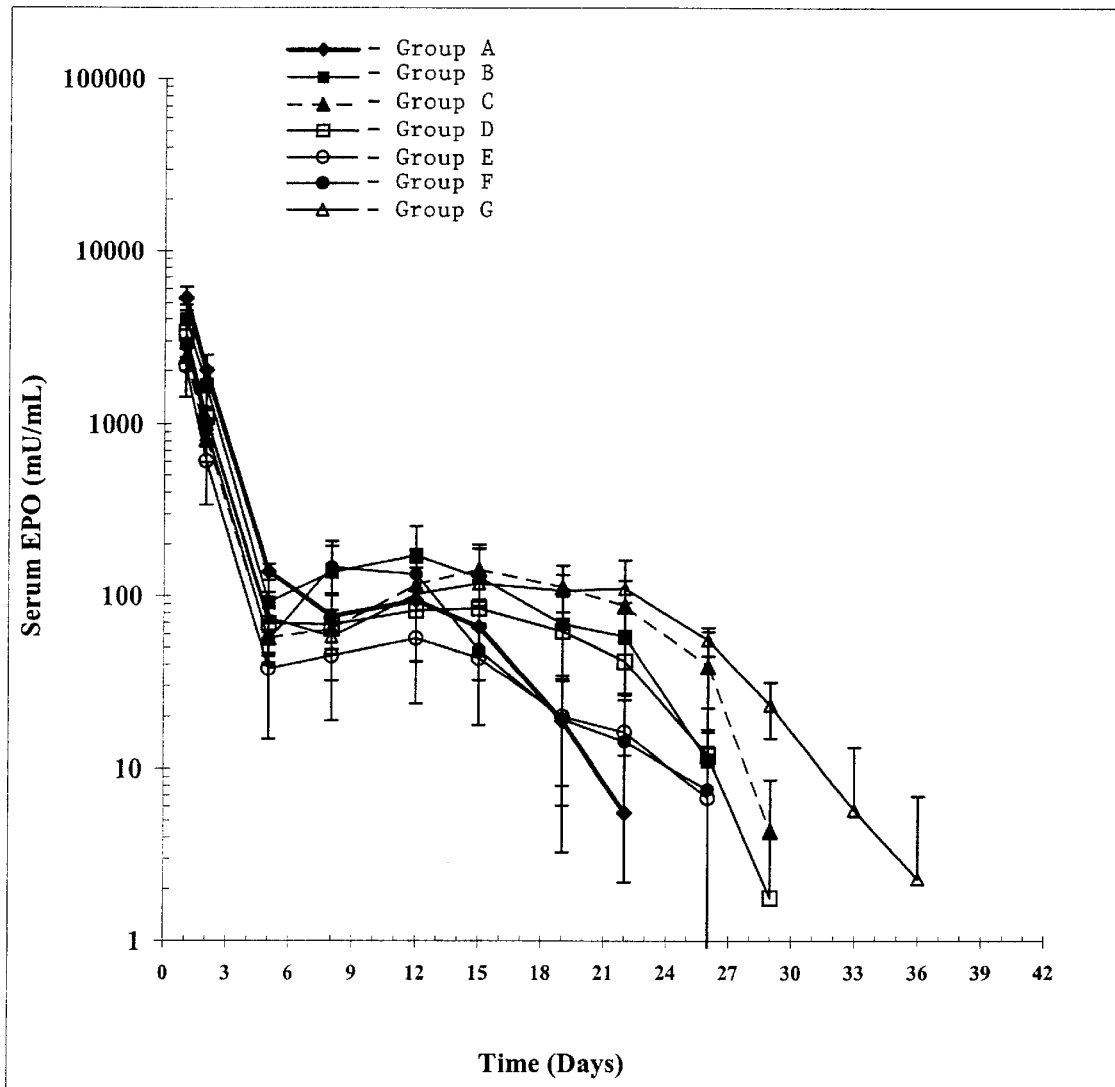
FIG. 1 is a plot of the serum EPO levels (mU/mL) versus time in days post administration of the EPO-containing and bisphosphonate-containing microparticles of the invention.

A description of preferred embodiments of the invention follows.

The present invention relates to a method for the sustained release in vivo of a biologically active agent comprising administering to a subject in need of treatment an effective amount of a sustained release composition comprising a biocompatible polymer having the biologically active agent incorporated therein, and a bisphosphonate wherein the bisphosphonate is present in an amount sufficient to modify the release profile of the biologically active agent from the sustained release composition.

In one embodiment, the bisphosphonate compound can be co-incorporated into the sustained release composition comprising the biocompatible polymer and the biologically active agent incorporated therein.

In another embodiment, the bisphosphonate compound can be separately incorporated into a second biocompatible polymer. The biocompatible polymer can be the same or different from the first biocompatible polymer which has the biologically active agent incorporated therein.

In yet another embodiment, the bisphosphonate compound can be present in an unencapsulated state but comingled with the sustained release composition. For example, the bisphosphonate can be solubilized in the vehicle used to deliver the sustained release composition. Alternatively, the bisphosphonate compound can be present as a solid suspended in an appropriate vehicle. Further, the bisphosphonate can be present as a powder which is comingled with the sustained release composition.

Bisphosphonates are a group of synthetic pyrophosphates characterized by a P-C-P type backbone. The bisphosphonates are potent inhibitors of bone resorption and ectopic calcification. In general the bisphosphonates can be represented by Formula I:

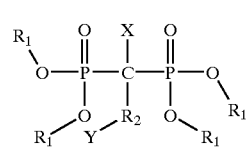

wherein, $R_1$ is independently, H, alkyl, aryl or heteroaryl;

X is H, —$OR_1$ or halogen;

$R_2$ is H, O, S, N, $(CH_2)_n$, branched alkylene, branched or straight alkenylene or alkynylene;

n is an integer from about 0 to about 18;

Y is H, $R_1$, halogen, amino, cyano or amido group.

As used herein, "alkyl" refers to a straight chain or branched, substituted or unsubstituted $C_1$–$C_{18}$ hydrocarbon group. Examples of suitable alkyl groups include, but are not limited to, methyl, ethyl, propyl, butyl, pentyl, isopropyl, isobutyl, and tert-butyl. As used herein, "halogen" refers to chlorine, bromine, iodine and fluorine. The term "aryl" as used herein refers to unsubstituted and substituted aromatic hydrocarbons. The term "heteroaryl" as used herein refers to unsubstituted or substituted aryl groups wherein at least one carbon of the aryl group is replaced with a heteroatom (e.g., N, O or S). Suitable substituents, include, for example, but are not limited to, halogen, —OH, alkoxy, amino, amido, —SH, cyano, —$NO_2$, —COOH, —COH, —$COOR_1$.

A number of geminal bisphosphonates such as those shown below are currently used for the treatment of moderate to severe Paget's disease and hypercalcemia associated with malignant neoplasms, treatment of osteolytic bone lesions associated with multiple myeloma and treatment of osteoporosis.

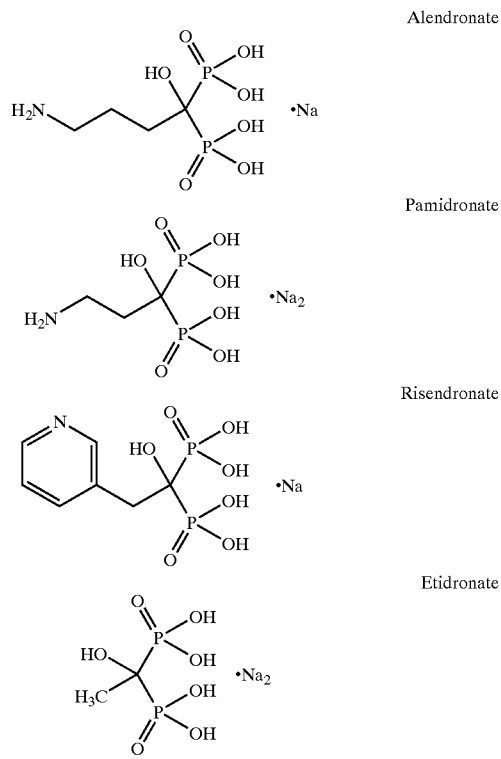

-continued

Tiludronate

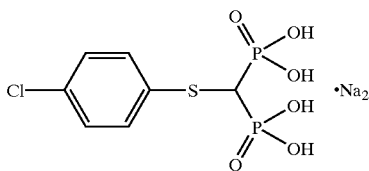

Bisphosphonates suitable for use in the invention include those described in U.S. Pat. No. 4,705,651, U.S. Pat. No. 4,327,039, U.S. Pat. No. 5,312,954 and U.S. Pat. No. 5,196,409 to Breuer et al., U.S. Pat. No. 5,412,141 to Nugent, U.S. Pat. Nos. 4,922,007 and 5,019,651 to Kieczykowski et al., U.S. Pat. No. 5,583,122 to Benedict et al., U.S. Pat. No. 6,080,779 to Gasper et al., U.S. Pat. No. 6,117,856 to Benderman et al., U.S. Pat. No. 6,162,929 to Foricher et al. and U.S. Pat. No. 5,885,473 to Papapoulos et al. the entire content of all of which are hereby incorporated by reference.

"Patient" as that term is used herein refers to the recipient of the treatment. Mammalian and non-mammalian patients are included. In a specific embodiment, the patient is a mammal, such as a human, canine, murine, feline, bovine, ovine, swine or caprine. In a preferred embodiment, the patient is a human.

The term "sustained release composition" as defined herein, comprises a biocompatible polymer having incorporated therein at least one biologically active agent. Suitable biocompatible polymers, can be either biodegradable or non-biodegradable polymers or blends or copolymers thereof, as described herein.

Typically, the sustained release composition can contain from about 0.01% (w/w) to about 50% (w/w) of the biologically active agent (dry weight of composition). The amount of agent used will vary depending upon the desired effect of the agent, the planned release levels, and the time span over which the agent will be released. A preferred range of agent loading is between about 0.1% (w/w) to about 30% (w/w) agent. A more preferred range of agent loading is between about 0.5% (w/w) to about 20% (w/w) agent.

The sustained release compositions of this invention can be formed into many shapes such as a film, a pellet, a rod, a filament, a cylinder, a disc, a wafer or a microparticle. A microparticle is preferred. A "microparticle" as defined herein, comprises a polymer component having a diameter of less than about one millimeter and having a biologically active agent dispersed therein. A microparticle can have a spherical, non-spherical or irregular shape. Typically, the microparticle will be of a size suitable for injection. A preferred size range for microparticles is from about one to about 180 microns in diameter.

As defined herein, a sustained release of biologically active agent is a release of the agent from a sustained release composition. The release occurs over a period which is longer than that period during which a therapeutically significant amount of the biologically active agent, would be available following direct administration of a solution of the biologically active agent. It is preferred that a sustained release be a release of biologically active agent which occurs over a period of greater than two days. A sustained release of biologically active agent, from a sustained release composition can be a continuous or a discontinuous release, with relatively constant or varying rates of release. The continuity of release and level of release can be affected by the type of polymer composition used (e.g., monomer ratios, molecular weight, and varying combinations of polymers), agent loading, and/or selection of excipients to produce the desired effect.

As used herein, the term "a" or "an" refers to one or more.

As used herein, "sufficient bisphosphonate compound to modify the release profile of the biologically active agent from the biocompatible polymer" means that amount of bisphosphonate compound which modifies the release profile of the biologically active agent from the biocompatible polymer which occurs when the sustained release composition does not include a bisphosphonate compound.

"Modifies the release profile" as that term is used herein refers to a prolongation of the period in which a therapeutic amount of the biologically active agent is released from the biocompatible polymer. It has also been observed that the initial release of biologically active agent can be reduced when a bisphosphonate is present in the sustained release composition.

A modification of the release profile can be confirmed by appropriate pharmacokinetic monitoring of the patient's serum for the presence of the biologically active agent or pharmacodynamic monitoring of the patient to monitor the therapeutic effects of the agent upon the patient. For example, specific antibody testing, as is well known in the art, can be used to determine the concentration of certain biologically active agents in the patient's serum. An example of such testing is described herein for erythropoietin. Further, the therapeutic effect of the biologically active agent can be determined by monitoring the pharmocodynamic effects of the biologically active agent. For example, determination of the patient's hematocrit in response to administration of erythropoeitin, as described herein. Methods of monitoring pharmacodynamic effects can be selected based upon the biologically active agent being administered using widely available techniques.

As used herein, a "therapeutically effective amount", "prophylactically effective amount" or "diagnostically effective amount" is the amount of the sustained release composition needed to elicit the desired biological response following administration.

The polymers of the invention are biocompatible. Suitable biocompatible polymers, can be either biodegradable or non-biodegradable polymers or blends or copolymers thereof, as described herein.

Suitable biocompatible polymers, can be either biodegradable or non-biodegradable polymers or blends or copolymers thereof, as described herein. A polymer is biocompatible if the polymer and any degradation products of the polymer are non-toxic to the recipient and also possess no significant deleterious or untoward effects on the recipient's body, such as an immunological reaction at the injection site.

"Biodegradable", as defined herein, means the composition will degrade or erode in vivo to form smaller chemical species. Degradation can result, for example, by enzymatic, chemical and physical processes. Suitable biocompatible, biodegradable polymers include, for example, poly (lactides), poly(glycolides), poly(lactide-co-glycolides), poly(lactic acid)s, poly(glycolic acid)s, polycarbonates, polyesteramides, polyanydrides, poly(amino acids), polyorthoesters, poly(dioxanone)s, poly(alkylene alkylate)s, copolymers or polyethylene glycol and polyorthoester, biodegradable polyurethane, blends thereof, and copolymers thereof.

Suitable biocompatible, non-biodegradable polymers include non-biodegradable polymers selected from the group consisting of polyacrylates, polymers of ethylene-vinyl acetates and other acyl substituted cellulose acetates, non-degradable polyurethanes, polystyrenes, polyvinylchloride, polyvinyl flouride, poly(vinyl imidazole), chlorosulphonate polyolefins, polyethylene oxide, blends thereof, and copolymers thereof.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weight is of about 2,000 Daltons to about 2,000,000 Daltons.

In a particular embodiment, the polymer is biodegradable polymer or copolymer. In a more preferred embodiment, the polymer is a poly(lactide-co-glycolide)(hereinafter "PLG"). The PLG can have a lactide:glycolide ratio, for example, of about 10:90, 25:75, 50:50, 75:25 or 90:10 and a molecular weight of about 5,000 Daltons to about 70,000 Daltons.

The term "biologically active agent," as used herein, is an agent, or its pharmaceutically acceptable salt, which when released in vivo, possesses the desired biological activity, for example therapeutic, diagnostic and/or prophylactic properties in vivo. It is understood that the term includes stabilized biologically active agents as described herein.

Examples of suitable biologically active agents include proteins such as immunoglobulins, antibodies, cytokines (e.g., lymphokines, monokines, chemokines), interleukins, interferons, erythropoietin, nucleases, tumor necrosis factor, colony stimulating factors, insulin, enzymes (e.g. superoxide dismutase, plasminogen activator, etc.), tumor suppressors, blood proteins, hormones and hormone analogs (e.g., growth hormone, adrenocorticotropic hormone, and luteinizing hormone releasing hormone (LHRH)), vaccines (e.g., tumoral, bacterial and viral antigens), antigens, blood coagulation factors; growth factors; peptides such as protein inhibitors, protein antagonists, and protein agonists; nucleic acids, such as antisense molecules; oligonucleotides; and ribozymes. Small molecular weight agents suitable for use in the invention include, antitumor agents such as bleomycin hydrochloride, carboplatin, methotrexate and adriamycin; antibiotics such as gentamicin, tetracycline hydrochloride and ampicillin; antipyretic, analgesic and anti-inflammatory agents; antitussives and expectorants such as ephedrine hydrochloride, methylephedrine hydrochloride, noscapine hydrochloride and codeine phosphate; sedatives such as chlorpromazine hydrochloride, prochlorperazine hydrochloride and atropine sulfate; muscle relaxants such as tubocurarine chloride; antiepileptics such as sodium phenytoin and ethosuximide; antiulcer agents such as metoclopramide; antidepressants such as clomipramine; antiallergic agents such as diphenhydramine; cardiotonics such as theophillol; antiarrhythmic agents such as propranolol hydrochloride; vasodilators such as diltiazem hydrochloride and bamethan sulfate; hypotensive diuretics such as pentolinium and ecarazine hydrochloride; antidiuretic agents such as metformin; anticoagulants such as sodium citrate and sodium heparin; hemostatic agents such as thrombin, menadione sodium bisulfite and acetomenaphthone; antituberculous agents such as isoniazide and ethanbutol; hormones such as predniso lone sodium phosphate and methimazole; antipsychotic agents such as risperidone; and narcotic antagonists such as nalorphine hydrochloride.

In one embodiment, the biologically active agent is stabilized. The biologically active agent can be stabilized against degradation, loss of potency and/or loss of biological activity, all of which can occur during formation of the sustained release composition having the biologically active agent dispersed therein, and/or prior to and during in vivo release of the biologically active agent. In one embodiment, stabilization can result in a decrease in the solubility of the biologically active agent, the consequence of which is a reduction in the initial release of biologically active agent, in particular, when release is from a sustained release composition. In addition, the period of release of the biologically active agent can be prolonged.

Stabilization of the biologically active agent can be accomplished, for example, by the use of a stabilizing agent or a specific combination of stabilizing agents. The stabilizing agent can be present in the mixture. "Stabilizing agent", as that term is used herein, is any agent which binds or interacts in a covalent or non-covalent manner or is included with the biologically active agent. Stabilizing agents suitable for use in the invention are described in U.S. Pat. Nos. 5,716,644, 5,674,534, 5,654,010, 5,667,808, and 5,711,968, and co-pending U.S. patent application Ser. No. 08/934,830 to Burke et al., filed on Sep. 22, 1997 and U.S. patent application Ser. No. 09/104,549 to Burke, filed on Jun. 25, 1998, now U.S. Pat. No. 6,265,389 to Burke having an issue date of Jul. 24, 2001, the entire teachings of which are incorporated herein by reference.

For example, a metal cation can be complexed with the biologically active agent, or the biologically active agent can be complexed with a polycationic complexing agent such as protamine, albumin, spermidine and spermine, or associated with a "salting-out" salt. In addition, a specific combination of stabilizing agents and/or excipients may be needed to optimize stabilization of the biologically active agent.

Suitable metal cations include any metal cation capable of complexing with the biologically active agent. A metal cation-stabilized biologically active agent, as defined herein, comprises a biologically active agent and at least one type of metal cation wherein the cation is not significantly oxidizing to the biologically active agent. In a particular embodiment, the metal cation is multivalent, for example, having a valency of +2 or more. It is preferred that the metal cation be complexed to the biologically active agent.

Suitable stabilizing metal cations include biocompatible metal cations. A metal cation is biocompatible if the cation is non-toxic to the recipient, in the quantities used, and also presents no significant deleterious or untoward effects on the recipient's body, such as a significant immunological reaction at the injection site. The suitability of metal cations for stabilizing biologically active agents and the ratio of metal cation to biologically active agent needed can be determined by one of ordinary skill in the art by performing a variety of stability indicating techniques such as polyacrylamide gel electrophoresis, isoelectric focusing, reverse phase chromatography, and HPLC analysis on particles of metal cation-stabilized biologically active agents prior to and following particle size reduction and/or encapsulation. The molar ratio of metal cation to biologically active agent is typically between about 1:2 and about 100:1, preferably between about 2:1 and about 12:1.

Examples of stabilizing metal cations include, but are not limited to, $K^+$, $Zn^{+2}$, $Mg^{+2}$ and $Ca^{+2}$. Stabilizing metal cations also include cations of transition metals, such as $Cu^{+2}$. Combinations of metal cations can also be employed.

The biologically active agent can also be stabilized with at least one polycationic complexing agent. Suitable polycationic complexing agents include, but are not limited to, protamine, spermine, spermidine and albumin. The suitability of polycationic complexing agents for stabilizing biologically active agents can be determined by one of ordinary skill in the art in the manner described above for stabilization with a metal cation. An equal weight ratio of polycationic complexing agent to biologically active agent is suitable.

Further, excipients can be added to maintain the potency of the biologically active agent over the duration of release and modify polymer degradation. The excipients can be added to the dispersed system which is then atomized or can be added to the mixture which is subjected to fragmenting either before or after fragmentation of the dried substance to achieve particles of biologically active agent. Suitable excipients include, for example, carbohydrates, amino acids, fatty acids, surfactants, and bulking agents, and are known to those skilled in the art. An acidic or a basic excipient is also suitable. The amount of excipient used is based on ratio to the biologically active agent, on a weight basis. For amino acids, fatty acids and carbohydrates, such as sucrose, trehalose, lactose, mannitol, dextran and heparin, the ratio of carbohydrate to biologically active agent, is typically between about 1:10 and about 20:1. For surfactants the ratio of surfactant to biologically active agent is typically between about 1:1000 and about 2:1. Bulking agents typically comprise inert materials. Suitable bulking agents are known to those skilled in the art.

The excipient can also be a metal cation component which is separately dispersed within the polymer matrix. This metal cation component acts to modulate the release of the biologically active agent and is not complexed with the biologically active agent. The metal cation component can optionally contain the same species of metal cation, as is contained in the metal cation stabilized biologically active agent, if present, and/or can contain one or more different species of metal cation. The metal cation component acts to modulate the release of the biologically active agent from the polymer matrix of the sustained release composition and can enhance the stability of the biologically active agent in the composition. A metal cation component used in modulating release typically comprises at least one type of multivalent metal cation. Examples of metal cation components suitable to modulate release include or contain, for example, $Mg(OH)_2$, $MgCO_3$ (such as $4MgCO_3 \cdot Mg(OH)_2 \cdot 5H_2O$), $MgSO_4$, $Zn(OAc)_2$, $Mg(OAc)_2$, $ZnCO_3$ (such as $3Zn(OH)_2 \cdot 2ZnCO_3)ZnSO_4$, $ZnCl_2$, $MgCl_2$, $CaCO_3$, $Zn_3(C_6H_5O_7)_2$ and $Mg_3(C_6H_5O_7)_2$. A suitable ratio of metal cation component to polymer is between about 1:99 to about 1:2 by weight. The optimum ratio depends upon the polymer and the metal cation component utilized. A polymer matrix containing a dispersed metal cation component to modulate the release of a biologically active agent from the polymer matrix is further described in U.S. Pat. No. 5,656,297 to Bernstein et al. and co-pending U.S. patent application Ser. No. 09/056,566 filed on Apr. 7, 1998, now U.S. Pat. No. 5,912,015, the teachings of both of which are incorporated herein by reference in their entirety.

The invention described herein also relates to pharmaceutical compositions suitable for use in the invention. In one embodiment, the pharmaceutical composition comprises a sustained release composition comprising a biocompatible polymer having an effective amount of a biologically active agent incorporated therein, and an amount of bisphosphonate compound sufficient to modify the release profile of the biologically active agent from the sustained release composition.

In one embodiment, the bisphosphonate compound can be co-incorporated into the sustained release composition comprising the biocompatible polymer and the biologically active agent incorporated therein.

In another embodiment, the pharmaceutical composition comprises the sustained release composition comprising a first biocompatible polymer having incorporated therein an effective amount of a biologically active agent and a second biocompatible polymer having incorporated therein an amount of bisphosphonate which modifies the release profile of the biologically active agent from the first polymer. In a particular embodiment, the first and second polymers are the same type of polymer. In another embodiment, the first and second polymers are different.

In yet another embodiment, the bisphosphonate compound can be present in the pharmaceutical composition in an unencapsulated state. For example, the bisphosphonate compound can be comingled with the sustained release composition. In one embodiment, the bisphosphonate can be solubilized in the vehicle used to deliver the pharmaceutical composition. Alternatively, the bisphosphonate compound can be present as a solid suspended in an appropriate vehicle useful for delivering the pharmaceutical composition. Further, the bisphosphonate can be present as a powder which is comingled with the sustained release composition.

The present invention also relates to a composition for the sustained release of bisphosphonates. The sustained release composition comprises a biocompatible polymer matrix having a therapeutically effective amount of bisphosphonate incorporated therein. Further, the invention relates to a method for the sustained release in vivo of a bisphosphonate compound comprising administering to a subject in need of treatment a therapeutically effective amount of a sustained release composition comprising a biocompatible polymer and a bisphosponate compound.

In a particular embodiment, administration of the sustained release composition comprising a biocompatible polymer and a bisphosphonate can be to a joint, for example, the articular space of a joint. For example, the sustained release composition can be administered to the articular space of the knee, shoulder, ankle, hip etc . . .

The sustained release composition of the invention comprising a biocompatible polymer and a bisphosphonate compound can be used for the treatment of diseases associated with bone resorption or joint inflammation. For example, the sustained release composition having a biocompatible polymer and a bisphosphonate compound incorporated therein can be suitable for use as a treatment for rheumatoid arthritis, osteoporosis or Paget's disease.

A number of methods are known by which sustained release compositions (polymer/active agent matrices) can be formed. In many of these processes, the material to be encapsulated is dispersed in a solvent containing a wall forming material. At a single stage of the process, solvent is removed from the microparticles and thereafter the microparticle product is obtained.

Methods for forming a composition for the sustained release of biologically active agent are described in U.S. Pat. No. 5,019,400, issued to Gombotz et al., and issued U.S. Pat. No. 5,922,253 issued to Herbert et al. the teachings of which are incorporated herein by reference in their entirety.

In this method, a mixture comprising a biologically active agent, a biocompatible polymer and a polymer solvent is processed to create droplets, wherein at least a significant portion of the droplets contains polymer, polymer solvent and the active. These droplets are then frozen by a suitable means. Examples of means for processing the mixture to form droplets include directing the dispersion through an ultrasonic nozzle, pressure nozzle, Rayleigh jet, or by other known means for creating droplets from a solution.

Means suitable for freezing droplets include directing the droplets into or near a liquified gas, such as liquid argon or liquid nitrogen to form frozen microdroplets which are then separated from the liquid gas. The frozen microdroplets are then exposed to a liquid or solid non-solvent, such as ethanol, hexane, ethanol mixed with hexane, heptane, ethanol mixed with heptane, pentane or oil.

The solvent in the frozen microdroplets is extracted as a solid and/or liquid into the non-solvent to form a polymer/active agent matrix comprising a biocompatible polymer and a biologically active agent. Mixing ethanol with other non-solvents, such as hexane, heptane or pentane, can increase the rate of solvent extraction, above that achieved by ethanol alone, from certain polymers, such as poly(lactide-co-glycolide) polymers.

A wide range of sizes of sustained release compositions can be made by varying the droplet size, for example, by changing the ultrasonic nozzle diameter. If the sustained release composition is in the form of microparticles, and very large microparticles are desired, the microparticles can be extruded, for example, through a syringe directly into the cold liquid. Increasing the viscosity of the polymer solution can also increase microparticle size. The size of the microparticles which can be produced by this process ranges, for example, from greater than about 1000 to about 1 micrometers in diameter.

Yet another method of forming a sustained release composition, from a suspension comprising a biocompatible polymer and a biologically active agent, includes film casting, such as in a mold, to form a film or a shape. For instance, after putting the suspension into a mold, the polymer solvent is then removed by means known in the art, or the temperature of the polymer suspension is reduced, until a film or shape, with a consistent dry weight, is obtained.

A further example of a conventional microencapsulation process and microparticles produced thereby is disclosed in U.S. Pat. No. 3,737,337, incorporated by reference herein in its entirety, wherein a solution of a wall or shell forming polymeric material in a solvent is prepared. The solvent is only partially miscible in water. A solid or core material is dissolved or dispersed in the polymer-containing mixture and, thereafter, the core material-containing mixture is dispersed in an aqueous liquid that is immiscible in the organic solvent in order to remove solvent from the microparticles.

Another example of a process in which solvent is removed from microparticles containing a substance is disclosed in U.S. Pat. No. 3,523,906, incorporated herein by reference in its entirety. In this process a material to be encapsulated is emulsified in a solution of a polymeric material in a solvent that is immiscible in water and then the emulsion is emulsified in an aqueous solution containing a hydrophilic colloid. Solvent removal from the microparticles is then accomplished by evaporation and the product is obtained.

In still another process as shown in U.S. Pat. No. 3,691,090, incorporated herein by reference in its entirety, organic solvent is evaporated from a dispersion of microparticles in an aqueous medium, preferably under reduced pressure.

Similarly, the disclosure of U.S. Pat. No. 3,891,570, incorporated herein by reference in its entirety, shows a method in which solvent from a dispersion of microparticles in a polyhydric alcohol medium is evaporated from the microparticles by the application of heat or by subjecting the microparticles to reduced pressure.

Another example of a solvent removal process is shown in U.S. Pat. No. 3,960,757, incorporated herein by reference in its entirety.

Tice et al., in U.S. Pat. No. 4,389,330, describe the preparation of microparticles containing an active agent by a method comprising: (a) dissolving or dispersing an active agent in a solvent and dissolving a wall forming material in that solvent; (b) dispersing the solvent containing the active agent and wall forming material in a continuous-phase processing medium; (c) evaporating a portion of the solvent from the dispersion of step (b), thereby forming microparticles containing the active agent in the suspension; and (d) extracting the remainder of the solvent from the microparticles.

Without being bound by a particular theory it is believed that the release of the biologically active agent can occur by two different mechanisms. First, the biologically active agent can be released by diffusion through aqueous filled channels generated in the polymer matrix, such as by the dissolution of the biologically active agent, or by voids created by the removal of the polymer solvent during the preparation of the sustained release composition. A second mechanism is the release of the biologically active agent, due to degradation of the polymer. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; and the molecular weight of the polymer. These properties can affect hydrophilicity and crystallinity, which control the rate of hydration of the polymer.

By altering the properties of the polymer, the contributions of diffusion and/or polymer degradation to biologically active agent release can be controlled. For example, increasing the glycolide content of a poly(lactide-co-glycolide) polymer and decreasing the molecular weight of the polymer can enhance the hydrolysis of the polymer and thus, provides an increased biologically active agent release from polymer erosion.

The composition of this invention can be administered in vivo, for example, to a human, or to an animal, orally, or parenterally such as by injection, implantation (e.g., subcutaneously, intramuscularly, intraperitoneally, intracranially, and intradermally), administration to mucosal membranes (e.g., intranasally, intravaginally, intrapulmonary, buccally or by means of a suppository), or in situ delivery (e.g., by enema or aerosol spray) to provide the desired dosage of antigen or labile agent based on the known parameters for treatment with the particular agent of the various medical conditions.

While this invention has been particularly shown and described with references to preferred embodiments thereof, it will be understood by those skilled in the art that various changes in form and details may be made therein without departing from the scope of the invention encompassed by the appended claims.

Exemplifications

Materials and Methods

In vivo Testing

Male Sprague-Dawley Rats, weighing between 350 to 450 grams (Charles River Laboratories, Inc.) were used in the studies described below following acclimation in standard animal housing for at least seven days. Animals were treated with cyclosporin (Sandimmune, Sandoz; CS) 5 mg/kg ip daily for days 0–14 post administration of the sustained release composition and bisphosphonate, and then 3 times per week thereafter. In some instances, cyclosporin treatment was omitted for at least two non-consecutive days during the initial 0–14 day treatment. Administration of the EPO-containing microparticles and bisphosphonate compound is described in detail below.

Preparation of Epo-Containing Microparticles

Microparticles containing recombinant human Erythropoietin (EPO) were made following the procedure described in U.S. Pat. No. 5,716,644 issued on Feb. 10, 1998 to Zale et al., the entire content of which is hereby incorporated by reference. Specifically, the EPO-containing microparticles were prepared using a polymer purchased from Alkermes, Inc. of Cincinnati, Ohio having Cat No. 5050DL2A which is a poly(lactide-co-glycolide) 10 kD polymer having a lactide/glycolide ratio of 50:50. The biosphosphonate-containing microparticles were prepared using a poly(lactide-co-glycolide) 25 kD polymer having a lactide/glycolide ratio of 50:50 also available from Alkermes, Inc. of Cincinnati, Ohio and having Cat. No. 5050DL3A. The EPO was obtained from Johnson & Johnson, New Brunswick, N.J. and stabilized prior to encapsulation as described in U.S. Pat. No. 5,716,644 using an EPO loading of about 1.6% w/w of the total weight of stabilized EPO in the microparticles.

Preparation of Bisphosphonate-Containing Microparticles

Bisphosphonate-containing microparticles having both a 1% and 2.5% w/w of the final weight of the microparticle theoretical load of the indicated bisphosphonate were prepared using a poly(lactide-co-glycolide) Cat. No. 5050DL3 earlier described having a lactide:glycolide ratio of 50:50.

Briefly, the bisphosphonates are soluble in water and insoluble in organics, making phase separation a suitable method for use in preparing the bisphosphonate-containing microparticles. First 212 mg of the poly(D,L-lactide-co-glycolide), with a molecular weight of about 25 kD available from Alkermes, Inc. of Cincinnati, Ohio, as Cat. No. 5050DL3A was weighed out and dissolved in methylene chloride at a concentration of about 5.9% W/V. 90 mg pamidronate disodium in 375 mg mannitol (available as AREDIA 90®) was weighed out and dissolved in about 3 g water. The encapsulate solution was then added to the polymer solution, and probe sonicated using pulses for about 1 minute to generate an extremely fine water-in-oil (W/O) emulsion.

The resulting emulsion was charged to a 350 mL glass reactor. The stir speed was set to about 1000 RPM. The coacervation agent, Dow Corning 360 Fluid, 350 cs, was slowly added by peristaltic pump to the stirring W/O emulsion to induce phase separation. Dow Corning 360 Fluid addition was halted when a 1:1 ratio of fluid to methylene chloride ratio had been achieved. Then the bottom stopcock of the reactor was opened in order to gravity feed embryonic microparticles into a heptane quench. After stirring for about 2 hours in the heptane quench, the hardened microparticles were isolated by filtration and allowed to dry in an ambient temperature vacuum chamber overnight. The product was then collected and weighed.

EXAMPLE 1

Pharmacological Effects of Bisphosphonate-Containing Microparticles on Epo Release from Epo-Containing Micro Following Co-Administration The Phamacokinetic (PK)/Pharmacodynamic (PD) response to EPO released from EPO-containing microparticles when co-administered with bisphosphonate-containing microparticles in vivo to male Sprague-Dawley rats was determined.

Microparticle Administration

Animals were anesthetized with 5% halothane. Each animal was shaved and the back swabbed with alcohol. Microparticles were resuspended using 0.75 mL vehicle (3% carboxymethylcellulose, 0.1% Tween 20, 0.9% NaCl, pH ~6). The microparticles were injected into an interscapular site using a 21 guage thinwall needle attached to a 1 mL syringe. Animals were dosed to receive a total of 10,000 U EPO in combination with a total of 2.5 mg of the indicated bisphosphonate. The amount of bisphosphonate-containing microparticles needed was determined based on the theoretical load of bisphosphonate in the microparticle formulation. For example, 100 mg of bisphosphonate-containing microparticles have a 2.5% theoretical load of bisphosphonate resulted in administration of 25 mg. Animals were followed for 47 days post implantation, except for Group G (Alendronate), which was followed for 57 days. The microparticles mixed and administered as one injection.

Bisphosphonate-containing microparticles having a 2.5% theoretical load of bisphosphonate were prepared as described above with a 2.5% theoretical load using the following bisphosphonate comounds: pamidronate (AREDIA®, (3-amino-1-hydroxypropylidene) bispnosphonic acid) disodium salt), etidronate ((1-hydroxyethyledene)bisphophonic acid) disodium salt, DIDRONEL®), tiludronate ([[(4-chlorophenyl)thio] methylene]bisphosphonic acid disodium salt, SKELID®), risedronate ([1-hydroxy-2-(3-pyridinyl)ethylidene] bisphosphonic acid) monosodium salt, ACTONEL®), and alendronate ((4-amino-1-hydroxybutylidene)bisphosphonic acid) monosodium salt, FOSAMAX®). In addition, microparticles having no bisphosphonate compound incorporated therein (placebo) were prepared following the method outlined.

Sample Collection Timepoints (days)

pre-bleed, 1, 2, 5, 8, 12, 15, 19, 22, 26, 29, 33, 36, 40, 42, 47, 50, 54, & 57

TABLE 1

| Group | # of Animal per Group | EPO Dose (Units) | Bisphophonate Compound | Bisphosphonate Dose (mg) |
|---|---|---|---|---|
| A | 4 | 10,000 | — | — |
| B | 4 | 10,000 | Placebo Microparticles | — |
| C | 4 | 10,000 | Pamidronate (AREDIA ®) | 2.5 mg |
| D | 4 | 10,000 | Etidronate (DIDRONEL ®) | 2.5 mg |
| E | 4 | 10,000 | Tiludronate (SKELID ®) | 2.5 mg |
| F | 4 | 10,000 | Risedronate (ACTONEL ®) | 2.5 mg |
| G | 4 | 10,000 | Alendronate (FOSAMAX ®) | 2.5 mg |

Serum Evaluation

Serum samples (40 µL) were collected via tail vein on the following days relative to microparticle administration: pre-bleed, 1, 2, 5, 8, 12, 15, 19, 22, 26, 29, 33, 36, 40, 42, 47, 50, 54 and 57. After clotting, the samples were centrifuged and frozen at −70° C. Serum EPO levels were quantitated by ELISA (R&D Systems, Minneapolis, Minn. Cat. No. DEPOO). The results are presented graphically in FIG. 1.

Hematocrits were evaluated manually following centrifugation for 5 minutes at 8000 rpm (on four animals per group) using a capillary tube. Hematocrits were also determined at the following intervals relative to microparticle administration: pre-bleed, 1, 2, 5, 8, 12, 15, 19, 22, 26, 29, 33, 36, 40, 42, 47, 50, 54 and 57. The results are presented graphically in FIG. 2.

Animals were observed on a regular basis for any signs of abnormal behavior. Injection sites were observed on a regular basis for induration, weeping or erythema. Sites were observed on a weekly basis for blanching. Body weights were taken and recorded at each sample collection timepoint.

The experiment was terminated once EPO serum levels had fallen below the limit of quantitation.

Results

The dose normalized data from ELISA testing of serum EPO levels are shown in FIG. 1. The data show that each of the bisphosphonate compounds tested enhanced the release of EPO from EPO-containing microparticles in comparison to the group receiving only EPO-containing microparticles. However, alendronate alone was shown to significantly affect the duration of EPO release from EPO-containing microparticles in comparison to groups receiving placebo microparticles co-administered with EPO-containing microparticles. That is, the animals of Group G had measurable levels of serum EPO at day 29 (23.17±8.22). This was significant in comparison to the placebo treated controls which were below the limit of quantitation at $p<0.01$. Further, a significant reduction in burst was seen in the Group C animals (Cmax: 2072.73±437.8) when compared to Group B animals (Cmax: 3989.56±883.47, $p<0.05$). Although the pamidronate treatment (Group C), increased the duration of release of detectable levels of EPO, it was not significantly different from the placebo-treated group (group B).

Figure 2:
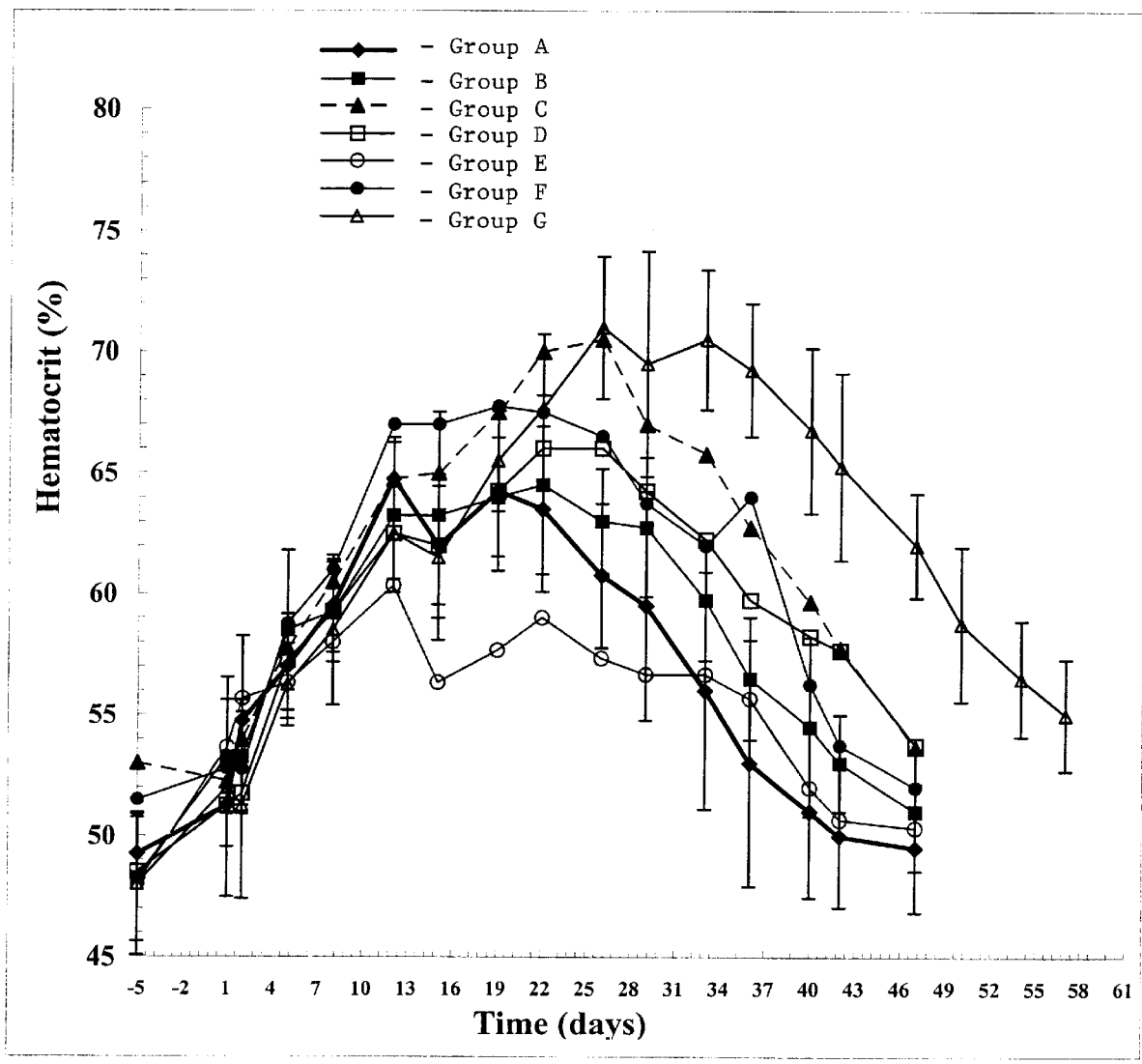
FIG. 2 is a plot of % hematocrit versus time in days post administration of the EPO-containing and bisphosphonate-containing microparticles of the invention.
Figure 3:
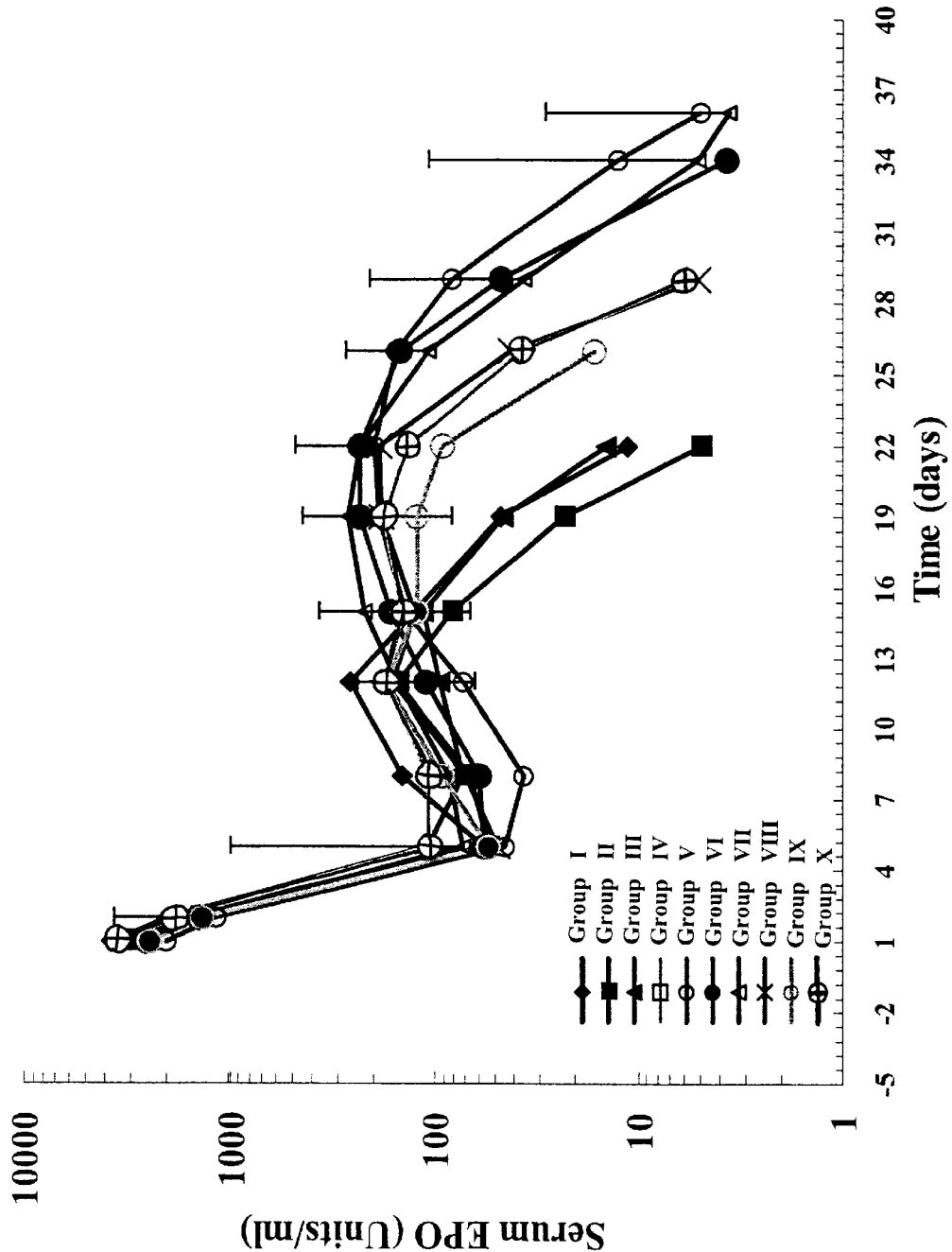
FIG. 3 is a plot of the serum EPO levels (mU/mL) versus time in days post administration of the EPO-containing and alendronate-containing microparticles of the invention.

Hematocrits in 4 out of 5 of the treated groups rose above that of the control groups A and B. Further, it was observed for Group G (alendronate) that the hematocrits remained significantly higher than controls past day 36 (FIG. 2). Day 36 is the last day serum levels of EPO were positive. The Alendronate treated group demonstrated higher hematocrits out to Day 47 which is the last day measured for control Groups A and B, demonstrating that the pharmacodynamic (PD) response extended out beyond pharmacokinetic (PK) response. In addition, at timepoints 26, 33 and 36 days, the hematocrits in the the Group C animals (pamidronate treated) were also significantly higher than controls ($p<0.05$). Following day 26, the hematocrits of all groups, with the exception of Group G, had reached baseline or near baseline levels. That is, Group G had significantly higher hematocrits than controls at all time points between day 26 and 47 ($p<0.05$) and did not approach baseline until day 57. Finally, comparing 60% hematocrits, the alendronate extended the PD response to EPO from day 32 in the placebo control group (B) to day 49. This is a 17-day enhancement using alendronate.

Pamidronate disodium (AREDIA®) in mannitol was dosed at 1 mg and admixed with EPO-containing microparticles.

In the group that received pamidronate in the vehicle (Group E) there was also an increase in duration of release. Group E also showed a significant elevation of release in the day 12 to day 15 timepoints relative to other groups. This enhanced release can be useful in clinical settings where tailored release is desired.

The use of pamidronate in vehicle (group E) also enhanced EPO PK/PD

EXAMPLE 2

Co-Administration of Epo-Containing Microparticles with Alendronate-Containing Microparticles at Varying Doses This example compares the PK/PD response to EPO released from EPO-containing microparticles when co-administered with various doses of alendronate-containing microparticles.

Materials and Methods

EPO-containing microparticles, alendronate-containing microparticles and placebo microparticles were prepared as described in Example 1. Alendronate-containing microparticles were prepared at a loading of 1.0% and 2.5% (theoretical). Microparticle administration, sample collection and sample analysis were as described in Example 1 and are summarized in Table 2. Sample collection timepoints were pre-bleed, 1, 2, 5, 8, 12, 15, 19, 22, 26, 29, 33, 36, 40.

TABLE 2

| Group | Number of Animals per Group | Epo Dose (U) | Alendronate Dose (mg) (theoretical load × mg μparticles = dose) | Placebo Dose (mg) |
|---|---|---|---|---|
| I | 4 | 10,000 U | — | 100 mg |
| II | 4 | 10,000 U | — | 50 mg |
| III | 4 | 10,000 U | — | 25 mg |
| IV | 4 | — | 2.5 mg (2.5% × 100 mg μparticles) | — |
| V | 4 | 10,000 U | 2.5 mg (2.5% × 100 mg μparticles) | — |
| VI | 4 | 10,000 U | 1.25 mg (2.5% × 50 mg μparticles) | — |
| VII | 4 | 10,000 U | 0.625 mg (2.5% × 25 mg μparticles) | — |
| VIII | 4 | 10,000 U | 1.0 mg (1.0% × 100 mg μparticles) | — |
| IX | 4 | 10,000 U | 0.5 mg (1.0% × 50 mg μparticles) | — |
| X | 4 | 10,000 U | 0.25 mg (1.0% × 25 mg μparticles) | — |

Results:

Serum ELISA data show a clear dose response in animals that received the 1% and 2.5% alendronate encapsulated microspheres. FIG. 3 shows the pharmacokinetic profile over the study period out to 36 days. Serum EPO levels in animals of Groups I, II and III, receiving only EPO-containing microparticles and placebo microparticles (no bisphosphonate) at 100, 50 and 25 mg doses were not measurable after day 22. Groups VIII, IX and X which received 1% alendronate-containing microparticles with a total dose of 1.0, 0.5 and 0.25 mg declined by day 29. However, serum EPO levels in Groups V, VI and VII which received 2.5% loaded alendronate-containing microparticles for a total of 2.5, 1.25 and 0.625 mg of alendronate were detectable out to at least day 34.

Table 3 summarizes Cmax data for this study. The Cmax for Groups V and VI receiving 100 or 50 mg of the 2.5% loaded alendronate-containing microparticles for a total of 2.5 and 1.25 mg, respectively were significantly lower than the dose matched placebo Groups I and II ($p<0.05$). Cmax was not significantly suppressed for Group VII compared to the corresponding placebo control. Steady state levels (Day 5 to Day 29) for Groups VI and VII were increased from 48 to 132 and 56 to 146 relative to their controls ($p<0.05$). Groups VIII, IX and X (1% loaded microparticles) showed steady state serum EPO increases of 48 to 84 and 56 to 111 at the 25 and 50 mg doses, however these differences were not statistically significant compared to the placebo groups at the same doses of blank microparticles.

TABLE 3

| Group | | Cmax | Tmax | Ave Steady Stat |
|---|---|---|---|---|
| | 100 mg | | | |
| I | EPO + 100 mg Placebo | 3764.79 ± 425.06 | 1 | 81.17 ± 17.19 |
| V | EPO + 100 mg 2.5% Alendronate | 2003.31 ± 308.80 | 1 | 116.17 ± 24.18 |
| VIII | EPO + 100 mg 1.0% Alendronate | 2966.20 ± 530.14 | 1 | 103.60 ± 7.47 |
| | 50 mg | | | |
| II | EPO + 50 mg Placebo | 2968.51 ± 260.47 | 1 | 48.27 ± 14.83 |
| VI | EPO + 50 mg 2.5% Alendronate | 2538.13 ± 231.93 | 1 | 132.41 ± 24.90 |
| IX | EPO + 50 mg 1.0% Alendronate | 2464.98 ± 647.79 | 1 | 84.96 ± 35.89 |
| | 25 mg | | | |
| III | EPO + 25 mg Placebo | 3597.26 ± 247.76 | 1 | 56.48 ± 10.09 |
| VII | EPO + 25 mg 2.5% Alendronate | 2972.05 ± 823.56 | 1 | 146.92 ± 36.33 |
| X | EPO + 25 mg 1.0% Alendronate | 3452.95 ± 1132.84 | 1 | 111.79 ± 54.93 |

Figure 4A:
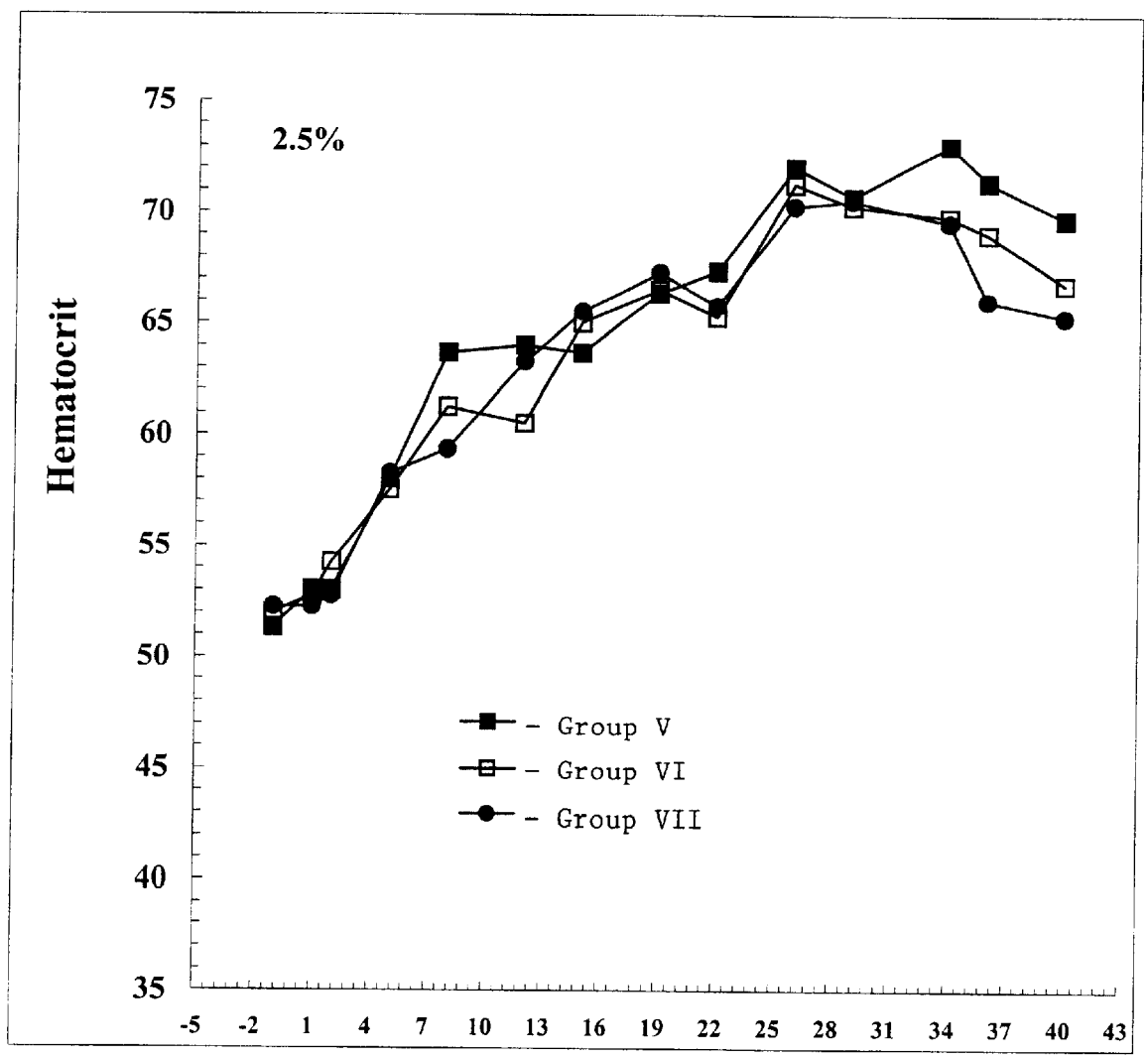
FIGS. 4A–4C are plots of % hematocrit versus time in days post administration of the EPO-containing and alendronate-containing microparticles of the invention.
Figure 4B:
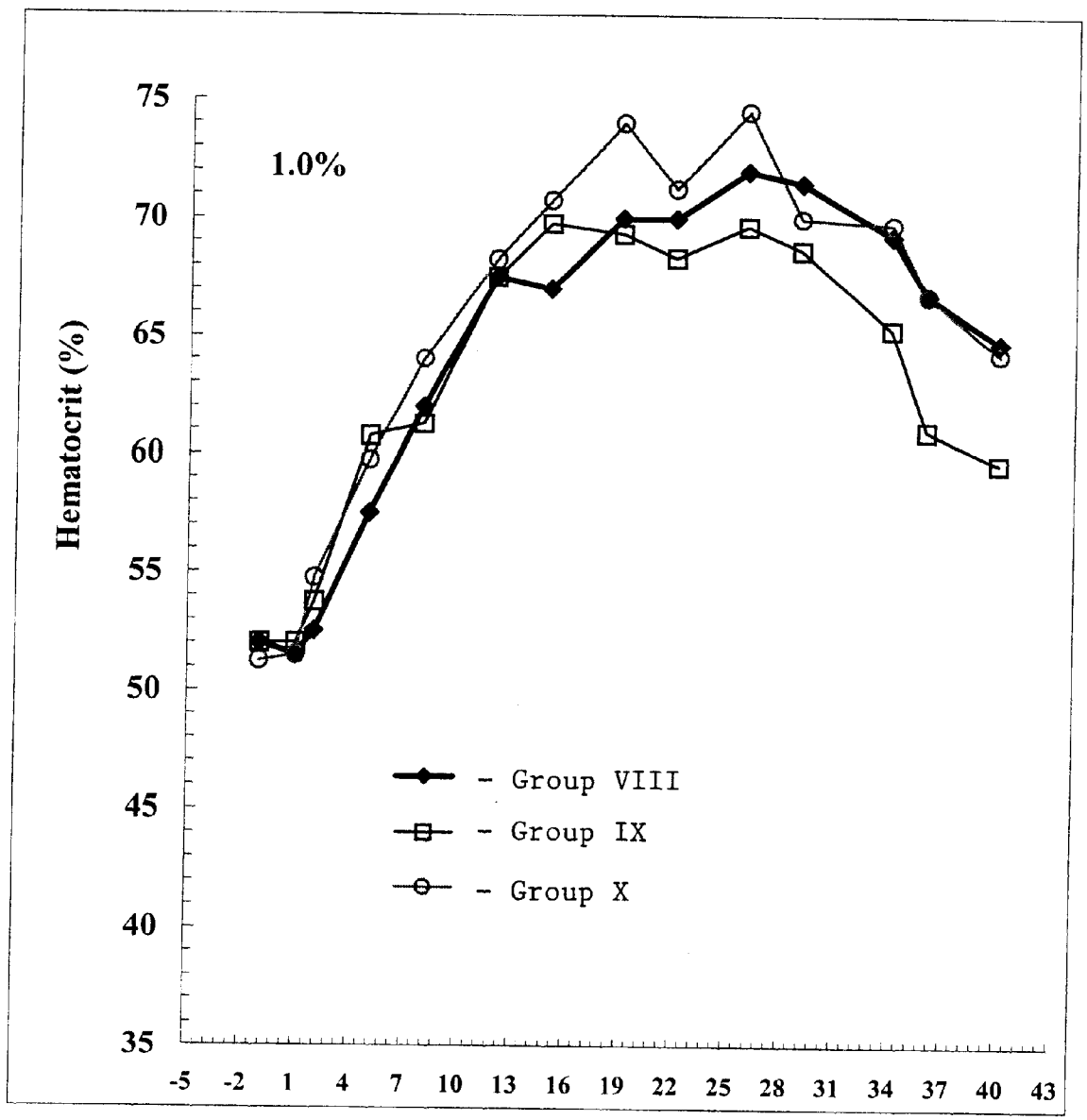
Figure 4C:
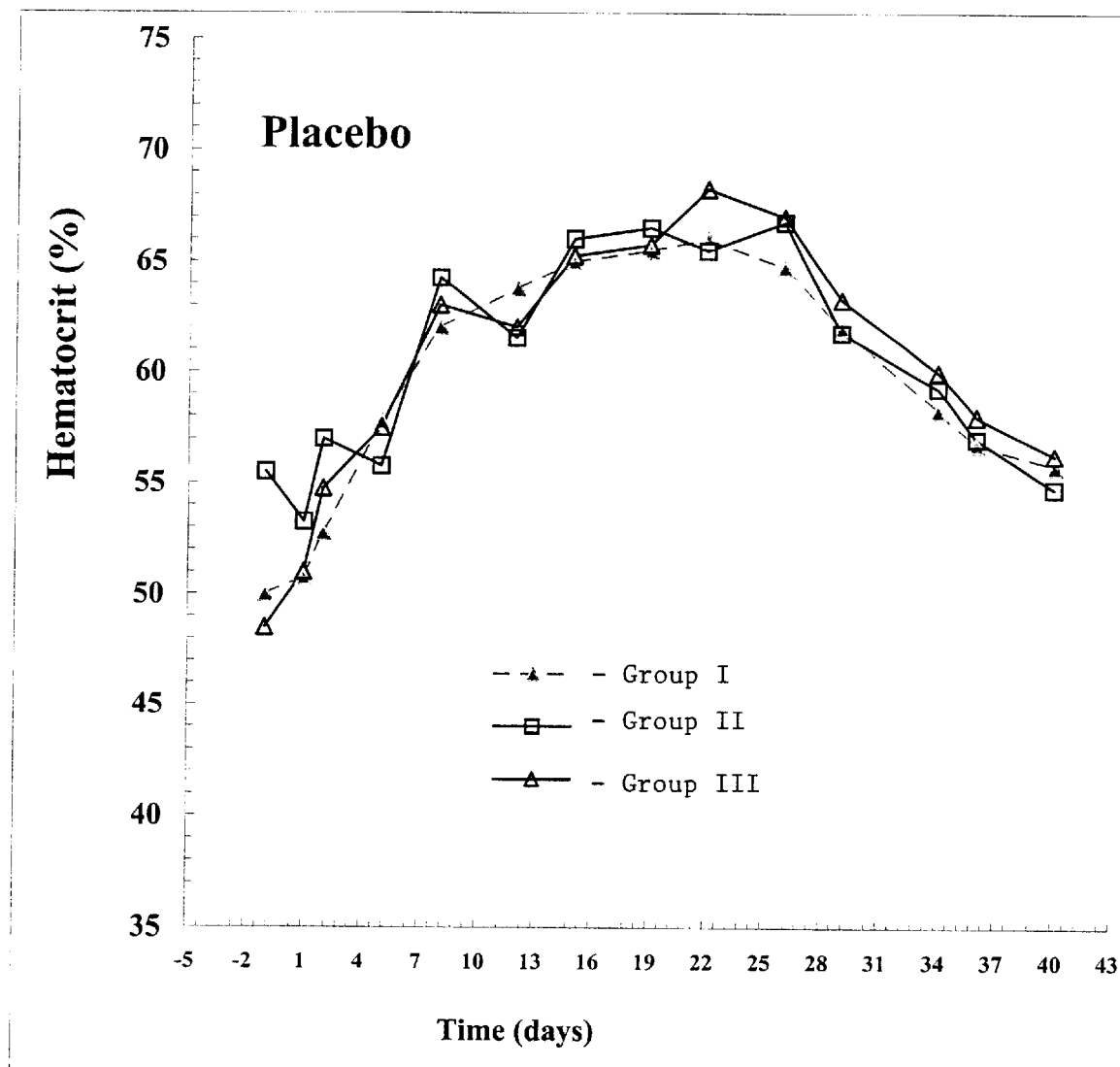

FIG. 4A shows an enhanced hematocrit response in rats to all three groups receiving varying doses of the 2.5% alendronate containing-microparticles co-administered with EPO containing-microparticles (Groups V, VI and VII) when compared to groups receiving the corresponding placebo dose of microparticles (FIG. 4C). The duration of hematocrits >60% was increased by at least 6 days in all groups. The complete enhancement effect on the pharmacodynamics could not be determined as a result of termination of the study at day 40.

The hematocrit levels for Groups V, VI and VII (FIG. 4A) were over 65% at day 40, significantly higher than controls (56%, P<0.01). FIG. 4B shows the hematocrit levels of the Groups VIII, IX and X treated with 100 mg, 50 mg or 25 mg of the 1% alendronate-containing microparticles, respectively co-administered with EPO containing-microparticles. Amongst Groups VIII, IX and X, only the 100 mg dose (Group VIII) was significantly higher at day 40 than the hematocrit value of the group receiving 100 mg of placebo microparticles co-administered with EPO-containing microparticles.

FIG. 4C represents hematocrit values obtained following injection with placebo microparticless co-administered with EPO-containing microparticles. It noted from FIGS. 4A–4C that there were no significant differences between hematocrits of the Groups receiving varying doses of 2.5% loaded alendronate-containing microparticles, receiving varying doses of 1.0% loaded alendronate-containing microparticles and varying doses of placebo microparticles when co-administered with EPO-containing microparticles.

Groups IV, V and VI (co-administration of 2.5% loaded alendronate-containing microparticles) as well as Group VIII (100 mg dose of the 1% alendronate-containing microparticles) had palpable masses at the injection sites at day 40. The study was terminated at this time to allow recovery of injection sites. There were no raised/inflammed sites in the placebo groups, however, which indicates that the inflammation was limited to the alendronate groups. Where there was a lower dose of microparticles, the size of the swelling was also smaller, and in the two lowest doses of alendronate (1% load, 50 and 25 mg doses) there were no palpable masses through the skin. Inflammation seen with alendronate groups is likely due to an acute phase response that can occur with amine containing bisphosphonates.

EXAMPLE 3
Effects of Pamidronate Co-Encapsulated with Epo Materials and Methods:

EPO-containing microparticles were prepared as described in Example 1 using a 40 kD Polymer poly(lactide-co-glycolide) polymer having a lactide glycolide ratio of 50:50 (Cat. No. 5050DL4A, Alkermes, Inc., Cinncinnati, Ohio). In addition, EPO-containing microparticles (1.9% theoretical load) having pamidronate co-encapsulated at nominal loads of 1% and 10% (theoretical) were also prepared as described in Example 1 for EPO alone.

Microparticle administration, sample collection and analysis were as described in Example 1 and are summarized in Table 4. Sample collection timepoints were pre-bleed, 1, 2, 6, 9, 13, 16, 20, 23, 27, 30, 34, 37, 41, 44, 48 days.

TABLE 4

| Group | # Animals per Group | Amount of EPO | Pamidronate (% Theoretical Load) |
|---|---|---|---|
| X | 5* | 20,000 U | — |
| Y | 5 | 20,000 U | 1% |
| Z | 5 | 20,000 U | 10% |

*Routine bleeds are taken from 5 of the animals in each group. Two animals from each group will be used for a histological assessment of the injection sites at the day 23 timepoint.

Figure 5:
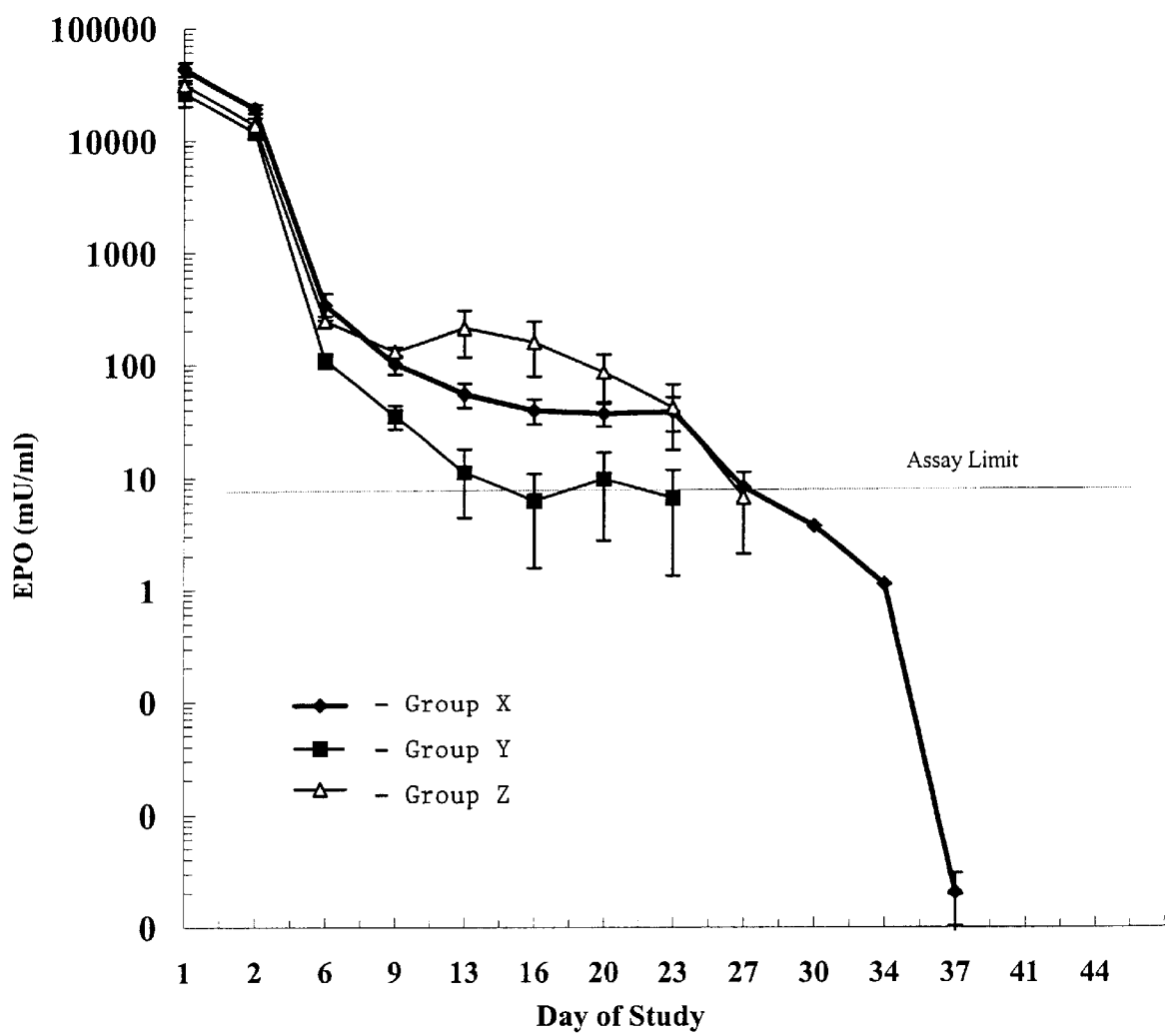
FIG. 5 is a plot of the serum EPO levels (mU/mL) versus time in days post administration of microparticles containing EPO and pamidronate co-encapsulated (1% and 10% load).

Results:

Following an initial peak at nearly 10,000 mU/mL or above, serum EPO levels in all groups decreased sharply until day 6, when a steady-state was reached at approximately 100 mU/ml (FIG. 5). However, serum EPO levels in groups which had been treated with EPO-containing microparticles co-encapsulated with 1% pamidronate began to decrease more rapidly such that the levels were at the assay detection limit by day 16. While serum EPO levels were elevated over controls with the microparticles containing EPO and 10% pamidronate, levels did not remain above controls after day 23. The serum EPO steady state level of the groups compared over day 9 through 27 showed a significant increase (p<0.05) in the group receiving 10% pamidronate-containing microparticles (Table 5) compared to the control group. Neither 1% or 10% containing pamidronate microparticles lowered EPO burst significantly, nor did it extend the steady state levels of EPO longer than control animals.

TABLE 5

| | EPO-Containing Microparticles 20,000 U | EPO, 20,000 U Pamidronate 1% | EPO, 20,000 U Pamidronate 10% |
|---|---|---|---|
| Cmax, mU/mL | 43090.42 | 26308.30 | 31472.63 |
| Tmax, day | 1.00 | 1.00 | 1.00 |
| AUC 0–1 d mU day/mL | 21545.21 | 10718.10 | 11249.28 |
| AUC 0–3 d, mU day/mL | 52655.19 | 26229.50 | 24860.95 |
| AUC d33, mU day/mL | 97692.89 | 61599.38 | 63330.36 |
| AUC (0–1)/(0–last) % | 22.84 | 24.87 | 22.29 |
| AUC (0–3)/(0–last) % | 56.22 | 59.59 | 46.79 |
| Average steady state value (days 9–27): | 54.12 | 13.82 | 125.64 |

Figure 6:
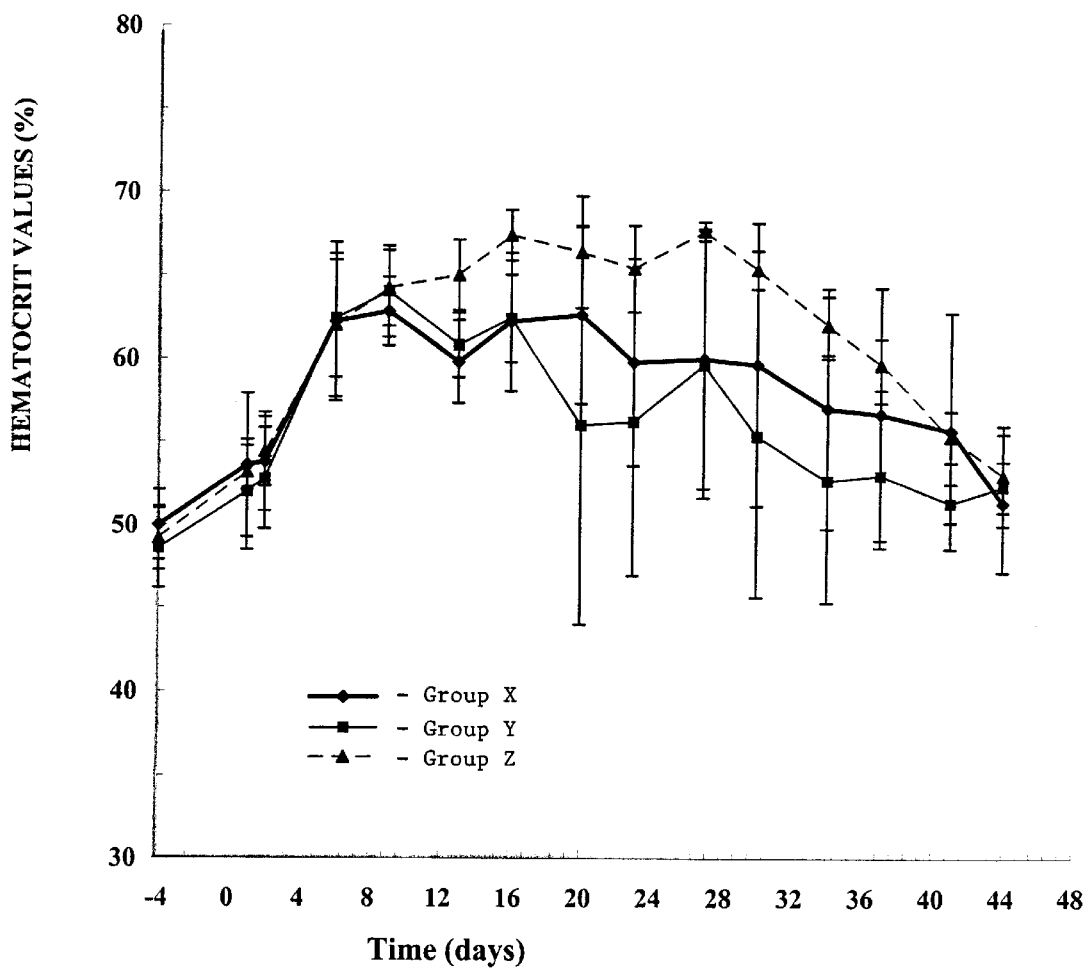
FIG. 6 is a plot of % hematocrit versus time in days post administration of microparticles containing EPO and pamidronate co-encapsulated (1% and 10% load).

Hematocrits were evaluated in the Groups X, Y and Z as a measure of the pharmacodynamic effect of EPO (FIG. 6). No significant effects were observed in the group receiving 1% bisphosphonate relative to controls. When animals received 10% bisphosphonate incorporated within EPO-containing microparticles, hematocrits showed an upward trend over the time period between 9 to 37 days. The difference in hematocrits is statistically different from controls on days 13 and 16 ($p<0.05$). This is consistent with the enhanced PK values for the group receiving 10% bisphosphonate observed between days 13 and 20.

The bisphosphonate, pamidronate was able to modulate both PK and PD responses to EPO when co-encapsulated into ProLease microspheres at a 10% nominal load. In this example, no increase in persistence of EPO responses was observed. However, the pamidronate did cause an elevation of EPO circulating serum levels for approximately one week. This increase is also reflected in enhanced pharmacodynamic responses.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for the sustained release in vivo of a biologically active agent selected from a biologically active protein, peptide or nucleic acid comprising administering to a subject in need of treatment an effective amount of a sustained release composition comprising a biocompatible polymer having a biologically active protein, peptide or nucleic acid incorporated therein, and a bisphosphonate compound wherein the bisphosphonate compound is present in an amount sufficient to modify the release profile of the biologically active protein, peptide or nucleic acid from the sustained release composition.

2. The method of claim 1, wherein the bisphosphonate compound is co-incorporated into the sustained release composition.

3. A method for the sustained release in vivo of a biologically active agent comprising administering to a subject in need of treatment an effective amount of a sustained release composition comprising a biocompatible polymer having a biologically active agent incorporated therein, and a bisphosphonate compound wherein the bisphosphonate compound is separately incorporated into a second biocompatible polymer and is present in an amount sufficient to modify the release profile of the biologically active agent from the sustained release composition.

4. The method of claim 3, wherein the second biocompatible polymer is the same as the biocompatible polymer of the sustained release composition.

5. The method of claim 3, wherein the second biocompatible polymer is different from the biocompatible polymer of the sustained release composition.

6. A method for the sustained release in vivo of a biologically active agent comprising administering to a subject in need of treatment an effective amount of a sustained release composition comprising a biocompatible polymer having a biologically active agent incorporated therein, and a bisphosphonate compound wherein the bisphosphonate compound is unencapsulated but comingled with the sustained release composition and is present in an amount sufficient to modify the release profile of the biologically active agent from the sustained release composition.

7. The method of claim 3 wherein the biocompatible polymer of the sustained release composition is selected from poly(lactides), poly(glycolides), poly(lactide-co-glycolides), poly(lactic acid)s, poly(glycolic acid)s, polycarbonates, polyesteramides, polyanhydrides, poly (amino acids), polyorthoesters, poly(dioxanone)s, poly (alkylene alkylate)s, copolymers of polyethylene glycol and polyorthoester, polyurethanes, blends thereof, and copolymers thereof.

8. The method of claim 7 wherein the biocompatible polymer is a poly(lactide-co-glycolide).

9. The method of claim 3 wherein the bisphosphonate compound is alendronate, risendronate, pamidronate, etidronate, tiludronate or a combination thereof.

10. The method of claim 3, wherein the sustained release composition is in the form of microparticles.

11. The method of claim 1, wherein the biologically active agent is a peptide.

12. The method of claim 1 wherein the biologically active agent is a protein.

13. The method of claim 12 wherein the protein is erythropoietin.

14. A pharmaceutical composition comprising:
  a) a sustained release composition comprising a biocompatible polymer having an effective amount of a biologically active agent selected from a biologically active protein, peptide or nucleic acid incorporated therein; and
  b) a bisphosphonate compound, wherein the bisphosphonate compound is present in an amount sufficient to modify the release profile of the biologically active protein, peptide or nucleic acid from the sustained release composition.

15. The pharmaceutical composition of claim 14, wherein the bisphosphonate compound is co-incorporated into the sustained release composition.

16. A pharmaceutical composition comprising:
  a) a sustained release composition comprising a biocompatible polymer having an effective amount of a biologically active agent incorporated therein; and
  b) a bisphosphonate compound, wherein the bisphosphonate compound is separately incorporated into a second biocompatible polymer and present in an amount sufficient to modify the release profile of the biologically active agent from the sustained release composition.

17. The pharmaceutical composition of claim 16, wherein the second biocompatible polymer is the same as the biocompatible polymer of the sustained release composition.

18. The pharmaceutical composition of claim 16, wherein the second biocompatible polymer is different from the biocompatible polymer of the sustained release composition.

19. A pharmaceutical composition comprising:
  a) a sustained release composition comprising a biocompatible polymer having an effective amount of a biologically active agent incorporated therein; and b) a bisphosphonate compound, wherein the bisphosphonate compound is unencapsulated but comingled with the sustained release composition and present in an amount sufficient to modify the release profile of the biologically active agent from the sustained release composition.

20. The pharmaceutical composition of claim 16 wherein the biocompatible polymer of the sustained release composition is selected from poly(lactides), poly(glycolides), poly(lactide-co-glycolides), poly(lactic acid)s, poly(glycolic acid)s, polycarbonates, polyesteramides, polyanhydrides, poly(amino acids), polyorthoesters, poly(dioxanone)s, poly(alkylene alkylate)s, copolymers of polyethylene glycol and polyorthoester, polyurethanes, blends thereof, and copolymers thereof.

21. The pharmaceutical composition of claim 20 wherein the biocompatible polymer is a poly(lactide-co-glycolide).

22. The pharmaceutical composition of claim 16 wherein the bisphosphonate compound is alendronate, risendronate, pamidronate, etidronate, tiludronate or a combination thereof.

23. The pharmaceutical composition of claim 16, wherein the sustained release composition is in the form of microparticles.

24. The pharmaceutical composition of claim 14, wherein the biologically active agent is a peptide.

25. The pharmaceutical composition of claim 14, wherein the biologically active agent is a protein.

26. The pharmaceutical composition of claim 25, wherein the protein is erythropoietin.

27. The method of claim 1, wherein the bisphosphonate compound is separately incorporated into a second biocompatible polymer.

28. The method of claim 27, wherein the second biocompatible polymer is the same as the biocompatible polymer of the sustained release composition.

29. The method of claim 27, wherein the second biocompatible polymer is different from the biocompatible polymer of the sustained release composition.

30. The method of claim 1, wherein the bisphosphonate compound is unencapsulated but comingled with the sustained release composition.

31. The method of claim 1 wherein the biocompatible polymer of the sustained release composition is selected from poly(lactides), poly(glycolides), poly(lactide-co-glycolides), poly(lactic acid)s, poly(glycolic acid)s, polycarbonates, polyesteramides, polyanhydrides, poly(amino acids), polyorthoesters, poly(dioxanone)s, poly(alkylene alkylate)s, copolymers of polyethylene glycol and polyorthoester, polyurethanes, blends thereof, and copolymers thereof.

32. The method of claim 31 wherein the biocompatible polymer is a poly(lactide-co-glycolide).

33. The method of claim 1 wherein the bisphosphonate compound is alendronate, risendronate, pamidronate, etidronate, tiludronate or a combination thereof.

34. The method of claim 1, wherein the sustained release composition is in the form of microparticles.

35. The method of claim 3, wherein the biologically active agent is a protein.

36. The method of claim 3, wherein the biologically active agent is peptide.

37. The method of claim 6 wherein the biocompatible polymer of the sustained release composition is selected from poly(lactides), poly(glycolides), poly(lactide-co-glycolides), poly(lactic acid)s, poly(glycolic acid)s, polycarbonates, polyesteramides, polyanhydrides, poly(amino acids), polyorthoesters, poly(dioxanone)s, poly(alkylene alkylate)s, copolymers of polyethylene glycol and polyorthoester, polyurethanes, blends thereof, and copolymers thereof.

38. The method of claim 37 wherein the biocompatible polymer is a poly(lactide-co-glycolide).

39. The method of claim 6 wherein the bisphosphonate compound is alendronate, risendronate, pamidronate, etidronate, tiludronate or a combination thereof.

40. The method of claim 6, wherein the sustained release composition is in the form of microparticles.

41. The method of claim 6, wherein the biologically active agent is a protein.

42. The method of claim 6, wherein the biologically active agent is a peptide.

43. The pharmaceutical composition of claim 14, wherein the bisphosphonate compound is separately incorporated into a second biocompatible polymer.

44. The pharmaceutical composition of claim 43, wherein the second biocompatible polymer is the same as the biocompatible polymer of the sustained release composition.

45. The pharmaceutical composition of claim 43, wherein the second biocompatible polymer is different from the biocompatible polymer of the sustained release composition.

46. The pharmaceutical composition of claim 14, wherein the bisphosphonate compound is unencapsulated but comingled with the sustained release composition.

47. The pharmaceutical composition of claim 14 wherein the biocompatible polymer of the sustained release composition is selected from poly(lactides), poly(glycolides), poly(lactide-co-glycolides), poly(lactic acid)s, poly(glycolic acid)s, polycarbonates, polyesteramides, polyanhydrides, poly(amino acids), polyorthoesters, poly(dioxanone)s, poly(alkylene alkylate)s, copolymers of polyethylene glycol and polyorthoester, polyurethanes, blends thereof, and copolymers thereof.

48. The pharmaceutical composition of claim 47, wherein the biocompatible polymer is a poly(lactide-co-glycolide).

49. The pharmaceutical composition of claim 14, wherein the bisphosphonate compound is alendronate, risendronate, pamidronate, etidronate, tiludronate or a combination thereof.

50. The pharmaceutical composition of claim 14, wherein the sustained release composition is in the form of microparticles.

51. The pharmaceutical composition of claim 16, wherein the biologically active agent is a protein.

52. The pharmaceutical composition of claim 16, wherein the biologically active agent is peptide.

53. The pharmaceutical composition of claim 19 wherein the biocompatible polymer of the sustained release composition is selected from poly(lactides), poly(glycolides), poly(lactide-co-glycolides), poly(lactic acid)s, poly(glycolic acid)s, polycarbonates, polyesteramides, polyanhydrides, poly(amino acids), polyorthoesters, poly(dioxanone)s, poly(alkylene alkylate)s, copolymers of polyethylene glycol and polyorthoester, polyurethanes, blends thereof, and copolymers thereof.

54. The pharmaceutical composition of claim 53 wherein the biocompatible polymer is a poly(lactide-co-glycolide).

55. The pharmaceutical composition of claim 19 wherein the bisphosphonate compound is alendronate, risendronate, pamidronate, etidronate, tiludronate or a combination thereof.

56. The pharmaceutical composition of claim 19, wherein the sustained release composition is in the form of microparticles.

57. The pharmaceutical composition of claim 19, wherein the biologically active agent is a protein.

58. The pharmaceutical composition of claim 19, wherein the biologically active agent is a peptide.

* * * * *